United States Patent [19]

Brufani et al.

[11] Patent Number: 4,999,350
[45] Date of Patent: Mar. 12, 1991

[54] (RS)-2-(2,3-DIHYDRO-5-HYDROXY-4,6,7-TRIMETHYLBENZOFURANYL) ACETIC ACIDS AND 2-(2,3-DIHYDRO-5-ACYLOXY-4,6,7-TRIMETHYLBENZOFURANYL) ACETIC ACIDS AND ESTERS THEREOF, USEFUL AS MUCOREGULATOR AND ANTI-ISCHEMIC DRUGS

[75] Inventors: Mario Brufani, Rome; Stefano Ceccarelli, Frosinone; Patrizia Giannetti, Frosinone; Agnese Paesano, Frosinone; Romolo Scuri, Piacenza; Sergio Zanarella, Rome, all of Italy

[73] Assignee: Biomedica Foscama Industria Chimico-Farmaceutica S.p.A., Rome, Italy

[21] Appl. No.: 337,358

[22] Filed: Apr. 13, 1989

[30] Foreign Application Priority Data

Aug. 1, 1988 [IT] Italy .................. 21603 A/88

[51] Int. Cl.$^5$ ..................... A61K 31/34; C07D 307/80
[52] U.S. Cl. ..................... 514/210; 514/212; 514/228.2; 514/233.5; 514/255; 514/320; 514/422; 514/469; 540/480; 540/596; 544/153; 544/58.7; 544/376; 546/196; 548/525; 548/950; 549/462

[58] Field of Search ............ 549/462; 514/469, 233.5, 514/228.2, 255, 320, 422, 212, 210; 544/153, 376, 58.7; 546/196; 548/525, 950; 540/596, 480

[56] References Cited

U.S. PATENT DOCUMENTS 4,857,516 8/1989 Terao et al. .................. 549/462

FOREIGN PATENT DOCUMENTS 63-88173 4/1988 Japan .

OTHER PUBLICATIONS

Burton et al., J. Am. Chem. Soc., vol. 107, pp. 7053–7065 (1985).
Ingold et al., Febs Letters, vol. 205 (1), pp. 117–120 (Sep. 1986).

Primary Examiner—Mary C. Lee
Assistant Examiner—Bernard I. Dentz
Attorney, Agent, or Firm—Notaro & Michalos

[57] ABSTRACT

The present invention relates to (RS)-2-(2,3-dihydro-5-hydroxy-4,6,7-trimethylbenzofuranyl) acetic acids and 2-(2,3-dihydro-5-acyloxy-4,6,7-trimethylbenzofuranyl) acetic acids and esters thereof, the process for producing them and their relevant therapeutical use as mucoregulators and antiischemic agents.

5 Claims, No Drawings

(RS)-2-(2,3-DIHYDRO-5-HYDROXY-4,6,7-TRIMETHYLBENZOFURANYL) ACETIC ACIDS AND 2-(2,3-DIHYDRO-5-ACYLOXY-4,6,7-TRIMETHYLBENZOFURANYL) ACETIC ACIDS AND ESTERS THEREOF, USEFUL AS MUCOREGULATOR AND ANTI-ISCHEMIC DRUGS

FIELD AND BACKGROUND OF THE INVENTION

The present invention relates to (RS) (2,3-dihydro-5-hydroxy-4,6,7-trimethylbenzofuranyl) acetic acids and 2 (2,3-dihydro-5-acyloxy-4,6,7-trimethylbenzofuranyl) acetic acids and esters thereof, the process for producing them and their relevant therapeutical use as mucoregulators and antiischemic agents.

It is well-known that the damage caused by free radicals and oxidizing metabolites forming starting from oxygen under pathological conditions affect various organs including respiratory apparatus, the brain, and the heart, and are involved in the pathogenesis of inflammatory processes, blood platelet aggregation, tumoral processes, miocardial and cerebral necrosis.

In particular, as to the respiratory apparatus, oxygen free radicals contribute, by inactivation of the inhibitor of alpha-1-protease, to the genesis of pulmonary emphysema and to the amplification of inflammatory processes.

As to the central nervous system, the oxygen free radicals are important mediators of the tissural damages occuring during reperfusion after cerebral ischemia.

As to myocardial ischemia, the oxygen free radicals contribute to cause miocardial damages both during ischemia and during post-ischemic reperfusion.

Substances having antioxidizing and radical scavenger activity, by neutralizing oxygen reactive metabolites, can be useful therapeutical agents for the treatment of pulmunary emphysema and of the inflammatory processes of the mucous membranes of the respiratory apparatus and for the sequences of cerebral and cardiac infarct.

SUMMARY OF THE INVENTION

Some of the substances synthetized to this end and claimed in the present invention have resulted, surprisingly, to have mucolytic and mucoregulating activity.

The present invention relates to anti-oxidizing substances of the following formula (I)

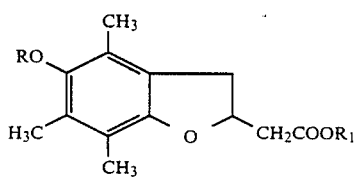

or to pharmaceutically acceptable salts thereof, wherein:

R is:
  a hydrogen,
  an acyl, either linear or branched, whith a number of carbon atoms variable from 1 to 7, in particular acetyl, propanoyl, butanoyl, isobutanoyl;
  a hemiacyl of a bicarboxylic acid, in particular hemisuccinoyl,
  an lower alkyl, in particular methyl and ethyl;

$R_1$ is:
  a hydrogen,
  a linear or branched alkyl with 1 to 20 carbon atoms, in particular methyl, ethyl, isobutyl, octyl, octadecyl,
  an alkyl ether of the type:

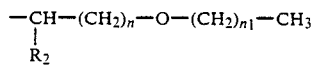

wherein n and $n_1$ are numbers variable from 0 to 6 and $R_2$ is an lower alkyl,
  an alkyl diether of the type:

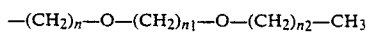

wherein n, $n_1$ are variable from 1 to 6 and $n_2$ is a number variable from 0 to 6,
  an alkylamine of the type:

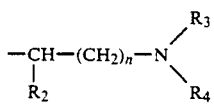

wherein n is a number variable from 0 to 6, $R_2$ has the previous meaning and $R_3$ and $R_4$ are lower alkyls: in particular the alkylamino group can be dimethylaminoethyl,
  a N-alkylheterocyclic of the type:

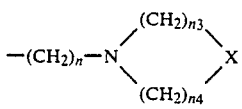

wherein $X=CH_2$, S, O, N—$R_2$ (wherein $R_2$ has the previous meaning), n is a number variable from 1 to 6, $n_3$ and $n_4$ are numbers variable from 1 to 3: in particular N-alkylheterocyclic can be a N-ethylmorpholinic or N-ethyl-N'-methylpiporazinic group.

The process for preparing the above described new compounds is also an object of the present invention (diagram 1). They are synthetized according to a general synthesis scheme using as starting product 2,5-diacetyloxy-3, 4,6-trimethylphenylacetaldehyde (prepared according to K.Okamoto et al., Chem.Pharm. Bull. 1082, (8), 2797) leading to obtain (Rs)-2-(2,3-dihydro-5-hydroxy-4,6,7-trimethylbenzofuranyl) acetic acid, in two steps. From the latter, by acylation and alkylation of the phenolic hydroxyl and by esterification of the carboxylic group with suitable reagents, all the products described in the present invention are obtained.

DESCRIPTION OF THE PREFERRED EMBODIMENT

In the first step a condensation according to Wittig is carried out between 2,5-diacetyloxy-3,4,6-trimethylphenylacetaldehyde and carboethoxymethylentriphenylphosphorane, dissolving the two compounds in a suitable organic solvent under stirring, bringing then the solution to boil and refluxing it for a sufficiently long time. By evaporation of the solvent, ethyl trans-4-

(2,5-diacetyloxy-3,4,6-trimethylphenyl)-2-butenoate is obtained, which is crystallized by a suitable solvent.

The latter, dissolved in an organic solvent, e.g. acetone, is saponified by treating it with KOH or NaOH, in the presence of sodic hydrosulphite or of another suitable reducer to prevent oxidation of the resulting hydroquinone to quinone, then refluxing the reaction mixture for a sufficiently long time. The thus formed hydroquinone cyclizes directly to a (RS)-2-(2,3-dihydro-5-hydroxy-4,6,7-trimethylbenzofuranyl)acetic acid, which is isolated by extraction with an organic solvent followed by re-extraction with a solution of NaHCO$_3$ and acidification of the latter. The product obtained is filtered under vacuum and crystallized.

out in an acetone solution using K CO q Na$_2$CO$_3$ as base and an alkyl halide.

The esterification of 5-acyl and 5-alkyl derivatives of (RS)-2-(2,3-dihydro-5-hydroxy-4,6, 7-trimethylbenzofuranyl) acetic acid is carried out passing through the acid halide thereof. To obtain the latter, the acid is dispersed in benzene and oxalyl halide is added, keeping then the solution under stirring, shortly, at a suitable temperature (generally 50° C.).

After removing the solvent and washing the residue with toluene, the halide is used directly, without purification, for the subsequent reaction. The latter consists in the esterification, carried out in an aprotic organic solvent such as tetrahydrofuran, by adding the alcohol

DIAGRAM 1

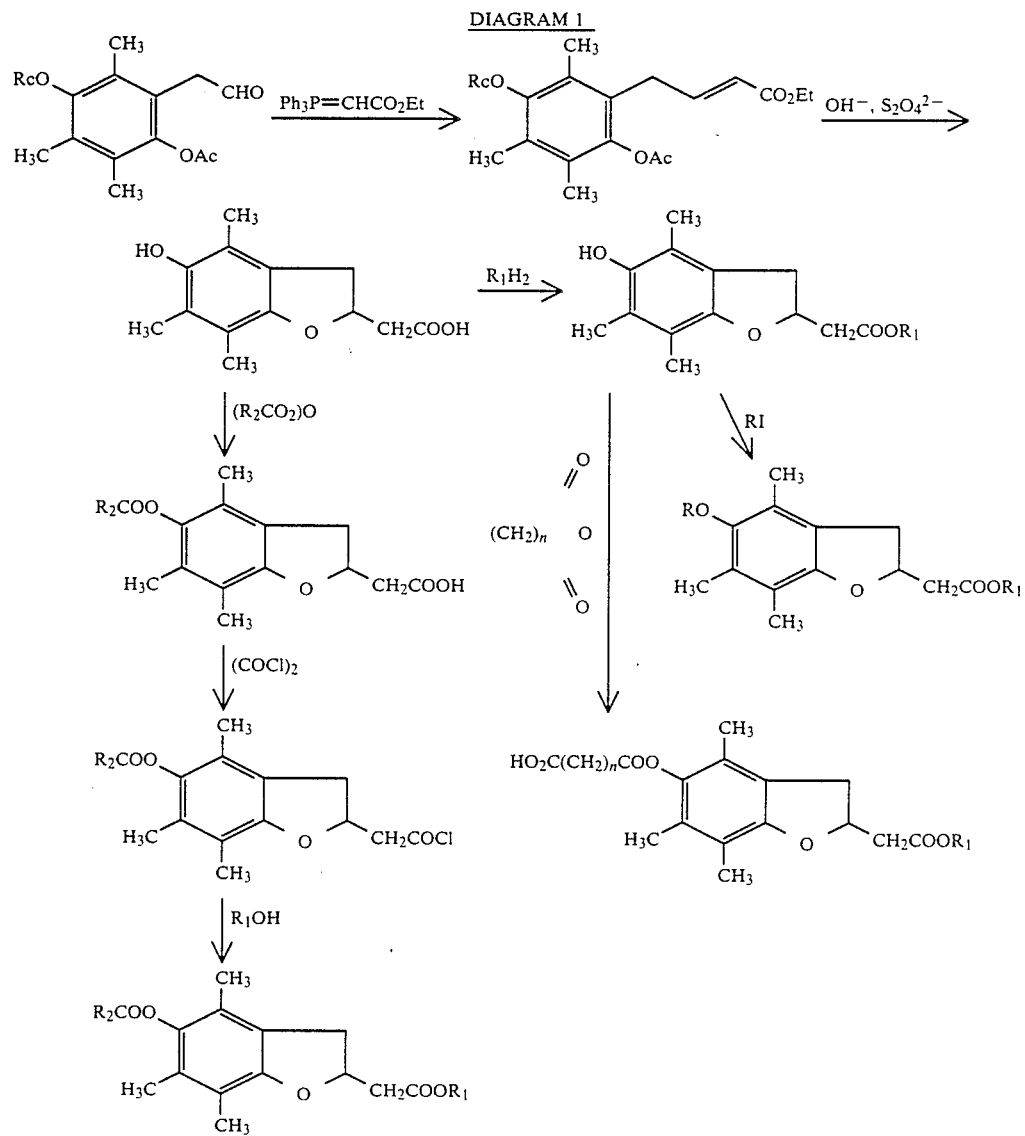

(RS)-2-(2,3-dihydro-5-hydroxy-4,6,7-trimethylbenzofuranyl) acetic acid is acylated to the phenolic hydroxyl dissolving it under nitrogen atmosphere in the sufficient amount of an organic base such as pyridine, collidine or toluidine and adding to such solution the acylating agent, i.e. the acid anhydride or an acylic halide. The reaction mixture, diluted with water, is then extracted with an organic solvent after acidification. The alkylation of the same phenolic hydroxyl is carried to the halide in the presence of pyridine or of another organic base. The isolation and purification of the final product depend on the nature of the alcohol used for the esterification.

Generally one extraction with organic solvent and one crystallization are sufficient. In some cases it is necessary to use chromatography tecniques.

It is possible, finally, to esterify directly (RS)-2-(2,3-dihydro-5-hydroxy-4,6,7-trimethylbenzofuranyl) acetic acid by reacting it with an ether solution, or in another organic solvent, of the suitable diazoalkane. Once the excess of the latter has been destroyed with acetic acid, the desired product is obtained by simply evaporating the solution and effecting a chromatography for the purification.

The invention also relates to the use of the substances of formula (I) as mucolytic-mucoregulating and antiinflammatory drugs.

In Table I there are reported, as an example, the effects on mucoproduction of the compounds:

(RS)-2-(2,3-dihydro-5-acetyloxy-4,6,7-trimethylbenzofuranyl) acetic acid (IRFI 016) and (RS)-2-(2,3-dihydro-5-hydroxy-4,6,7-trimethylbenzofuranyl) acetic acid (IRFI 005) and (RS)-2-(2,3-dihydro-5-acetyloxy-4,6,7-trimethylbenzofuranyl) acetic acid ethyl ester (IRFI 034).

In Table II there are reported the effects of compound IRFI 016 on muco production in rabbits.

In Table III there is reported the antiinflammatory activity of compound IRFI 016.

TABLE I: MUCOPRODUCTION IN MICE

The method described by Graziani et coll. (Il Farmaco Ed. Pr. 36, 167, 1981)—opportunely modified—has been followed.

Male albine mice CD 1 (Charles River) weighing 22-24 g. were used.

There was assessed the dosage of red phenol, injected intraperitoneally, in the bronchial wash liquid, comparing the values obtained in the treated animals.

The drugs were administered orally (gastric probing).

As comparison drugs some of the mucolytic/mucoregulating agents most widely known and used in human therapy have been chosen.

TABLE I

| SUBSTANCE | Oral administration. (n = 10) | |
|---|---|---|
| | $DE_{50}$ mg/kg | SAFETY LIMITS 95% |
| IRFI 016 | 151.697 | 112.602–190.692 |
| IRFI 005 | 61.88 | 53.534–70.232 |
| IRFI 034 | 44.477 | 39.132–49.821 |
| THIOPRONINE | 155.75 | 134.389–176.518 |
| BROMEXINE | 177.06 | 170.872–183.252 |

TABLE II: MUCOPRODUCTION IN RABBITS

The method described by Scuri et Coll. (Boll. Chim. Farm. 119, 181, 1980) was followed.

Male HY rabbits (Charles River) weighing 3-3.5 Kg were used.

The drugs were administered intravenously (auricular vein) and the tracheo-bronchial mucus was collected for 4 hours before (basal) and after the pharmaceutical treatment.

As comparison drugs some of the mucolitic/mucoregulating agents most known and used in human therapy were selected.

TABLE II

| SUBSTANCE | Intravenous administration (n = 10) | |
|---|---|---|
| | $DE_{50}$ mg/kg | SAFETY LIMITS |
| IRFI 005 | 12.443 | 8.827–16.060 |
| IRFI 016 | 10.547 | 8.723–12.372 |
| N-ACETYLCYSTEINE | 17.279 | 16.990–17.568 |
| BROMEXINE | 8.395 | 8.301–8.490 |
| SOBREROLE | 7.541 | 7.520–7.563 |

TABLE III: ANTINFLAMMATORY ACTIVITY

The method by Winter et Coll. (J.Pharmacol.Expl. The. 141, 369, 1963) was used.

Male Wistar rats (Charles River) weighing 120-130 g were used.

The influence of the drugs on the carragenine subplantar edema was studied (0.05 ml of a suspension of 1% carragenine in distilled water).

The drugs were administered orally (gastric probing).

TABLE III

| | Oral administration (n = 5) | | |
|---|---|---|---|
| SUBSTANCE | DOSAGE mg/kg | EDEMA VOL (ml) X + ES | VAR. % |
| CONTROLS | — | 0.332 + 0.45 | — |
| IRFI 016 | 200 | 0.158 + 0.38 | −52 |
| IRFI 016 | 100 | 0.202 + 0.43 | −39 |
| CONTROL | — | 0.310 + 0.05 | |
| PHENYLBUTAZONE | 100 | 0.140 + 0.02 | −58 |

Therefore, according to the present invention the compounds of formula I can be used as mucoregulating drugs for the treatment of all the diseases of the respiratory apparatus characterized by an increase in the consistence and amount of secretion (bronchitis and bronchiolitis, chronical bronchitis, bronchiectasis and complications of asthmatic disease and pulmunary emphysema, acute and chronical pharyngopharyngitis and tracheitis, rhinitis and synusitis with phlogosis of the mucous membrane of the respiratory tract).

For the therapeutical use the compounds of Formula I can be administered orally, topically, parenterally, by inhalation or rectally in formulations containing nontoxic conventional pharmaceutical excipients. The term 'parenteral' herein used includes subcutaneous, endovenous, intramuscular, intrasternum injections or technical infusions.

The pharmaceutical compostions containing the active principles can be in a form suitable to the oral use, e.g. tablets, aqueous or oily suspensions, dispersable powders or granules, hard or soft capsules, syrups or elixirs. The compositions for the oral use can contain one or more sweetening colouring aromatizing and preservative agents apt to make the pharmaceutical preparation elegant and palatable.

The formulations for the oral use include tablets wherein the active drug is mixed with non-toxic, pharmaceutically acceptable excipients that may be inert diluents such as calcium carbonate, sodium carbonate, lactose, calcium phosphate or sodium phosphate; granulating or disintegrating agents such as wheat starch or alginic acid; binding agents such as starch, jellies; lubricating agents such as magnesium stearate, stearic acid or talc.

The tablets can be non-coated or coated with the known techniques to retard disintegration and absorption in the gastrointestinal tract in order to have a delayed action, prolonged in time.

The aqueous solutions generally contain the active principles mixed with the suitable eccipients. The eccipients can be suspending agents, such as sodium carboxymethylcellulose, methylcellulose, hydroxypropylmethylcellulose, sodium alginate, polyvinylpyrrolidone; dispersing or wetting agents. They can contain one or more preservatives e.g. ethyl or n-propyl p-hydroxybenzoate; one or more colouring agents; one or more aromatizing agents; one or more sweeteners.

The oily suspensions can be formulated by suspending the active principle in a vegetal or mineral oil; they can contain sweetening and aromatizing agents to make the preparation palatable.

The dispersable powders and granules apt to the preparation of an aqueous suspension by addition of water contain the active principle in a mixture with a dispersing or wetting agent, a suspending agent and one or more preservatives.

The pharmaceutical compositions of the present invention can also be in the form of water/oil emulsion. The oily phase can be substituted by a vegetal or mineral oil. The emulsioning agents can be natural rubbers, such as acacia rubber, or natural phosphatides, e.g. lecitine or natural or synthetic fat acid esters.

Syrups and elixirs can be formulated with sweetening agents, e.g. glycerol, sorbitol or saccarose. The pharmaceutical compostions can be in the form of aqueous or oily sterile injectable suspensions. The suspensions can be formulated by the known techniques using dispersing or wetting agents and known suspending agents. The sterile injectable reparations can be sterile solutions or suspensions injectable in a non-toxic solvent or diluent suitable for parenteral use.

The compounds of Formula I can also be administered rectally in the form of suppositories. These compositions can be prepared by mixing the active principle with a suitable non-irritating eccipient which is solid at standard temperature but liquid at the rectal temperature; it melts, therefore, in the rectum and releases the drug. Polyethylenglycoles and cocoa butter are suitable to this end.

For the topic use creams, ointments, jellies, solutions, suspensions or other proper formulations containing the mucolytic can be prepared.

The following examples illustrate the invention without limiting it.

EXAMPLE 1

(a) Trans ethyl 4-(2,5-diacetyloxy-3,4,6-trimethylphenyl)-2-butenoate

A solution of 2.5-diacetyloxy-3,4,6-trimethylphenylacetaldehyde (69.1 g, prepared according to K.Okamoto et al, Chem.Pharm. Bull. 1982, 30, (8), 2797) and of carbohetoxymethylentriphenylphosphorane (145.2 g) is refluxed in dioxane (5.0 lt) for 16 hours. The mixture is evaporated under vacuum and the residue is crystallized by ethanol, obtaining 69.2 g of a white crystalline solid. M.P.=128 –30° C.; IR (KBr): 1750 ($CH_3COOAr$), 1724 cm$^{-1}$ ($COOC_2H_5$); $^1$H-NMR ($CDCl_3$): 7.2–6.7.(1H,m), 5.8–5.4 (1H,m), 4.15 (2H,q), 3.5–3.3 (2H,m), 2.30 (3H,s), 2.27 (3H,s), 2.02 (3H,s), 2.00 (6H,s), 1.2 (3H,t).

| Elemental analysis for $C_{19}H_{24}O_6$ (M.W. 348.39) | | | |
|---|---|---|---|
| | C % | H % | O % |
| Eval. | 66.09 | 6.82 | 27.08 |
| Found | 66.17 | 6.86 | 26.79 |

(b) (RS)-2-(2,3-dihydro-5-hydroxy-4,6,7-trimethylbenzofuranyl) acetic acid (IRFI 005)

A mixture of trans ethyl 4-(2,5-diacetyloxy-3,4,6-trimethylphenyl)-2-butenoate (69.2 g), $Na_2S_2O_4$ (210 g), acetone (850 ml) and 10% KOH (3.35 lt) is refluxed for 4 hours. After cooling, the solution is acidified and extracted with ethyl acetate. The organic phase is then washed twice with $H_2O$ and re-extracted with 5% $NaHCO_3$. The aqueous phase is acidified and the precipitate is vacuum filtered, dried and crystallized by benzene.

35.5 g is obtained. M.P.=173°–4° C.; IR (KBr): 3427 (OH), 1709 cm$^{-1}$ (COOH); $^1$H-NMR (DMSO-$d_6$): 12.2 (1H,sb), 7.4 (1H.sb), 5.35–4.85 (1H,m), 3.55–2.55 (4H,m), 2.05 (6H,s), 2.00 (3H,s),

| Elemental analysis for $C_{13}H_{16}O_4$ (M.W. 236.27) | | | |
|---|---|---|---|
| | C % | H % | O % |
| Eval. | 66.09 | 6.82 | 27.08 |
| Found | 66.17 | 6.86 | 26.79 |

EXAMPLE 2

(RS)-2-(2,3-dihydro-5-acetyloxy-4,6,7-trimethylbenzofuranyl) acetic acid (IRFI 016)

A solution of (RS)-2-(2,3-dihydro-5-hydroxy-4,6,7-trimethylbenzofuranyl) acetic acid (see example 1) (3.5 g) in pyridine (15.8 ml) and acetic anhydride (9.5 ml) is stirred under nitrogen atmosphere for 4 hours. To the solution there is added ice (40g) and HCl 6 N until pH 2, then is extracted with chlorophorm.

The organic phase is dried and vacuum evaporated. The residue is crystallized by benzene: 3.0 g of a white crystalline solid is obtained. M.P.=165°–6° C.; IR (KBr): 1749 ($CH_3COOAr$), 1706 (cm$^{-1}$) (COOH); $^1$H-NMR ($CDCl_3$) : 10.4 (1H,s), 5.35–4.85 (1H,m) 3.55–2.55 (4H,m), 2.30 (3H,s), 2.05 (3H,s), 2.00 (6H,s).

| Elemental analysis for $C_{15}H_{18}O_5$ (M.W. 278.30) | | |
|---|---|---|
| | C % | H % |
| Eval. | 64.74 | 6.52 |
| Found | 64.74 | 6.54 |

EXAMPLE 3

Propionic acid, 5-(2,3-dihydro-2-(RS)-carboxymethyl-4,6,7-trimethylbenzofuranyl) ester A solution of (RS)-2-(2,3-dihydro-5-hydroxy-4,6,7-trimethylbenzofuranyl) acetic acid (see example 1) (0.5 g) in pyridine (2.3 ml) with addition of propionic anhydride (1.8 ml) is stirred in inert atmosphere for 2 hours. To the solution are added ice (5 g) and HCl 6 N until pH 2: a white solid is thus precipitated. The product is vacuum filtered, dried and crystallized by benzene/heptane. 0.4 g of a white crystalline solid is obtained. M.P.=148°–50° C.; IR (KBr): 1746 (EtCOOAr), 1710 cm$^{-1}$ (COOH); $^1$H-NMR (CDCl$_3$): 11.0 (1H,sb), 5.35–4.85 (1H,m), 3.35–2.55 (6H,m), 2.0 (3H,s), 1.9 (6H,s), 1.2 (3H,t,J=14Hz)

| Elemental analysis for C$_{16}$H$_{20}$O$_5$ (M.W. 292.33) | | |
|---|---|---|
|  | C % | H % |
| Eval. | 65.74 | 6.89 |
| Found | 66.01 | 6.83 |

EXAMPLE 4

Succinic acid, mono 5-(2,3-dihydro-2-(RS)-carboxymethyl-4,6,7-trimethylbenzofuranyl) ester A mixture of (RS)-2-(2,3-dihydro-5-hydroxy-4,6,7-trimethylbenzofuranyl) acetic acid (see example 1) (1.0 g) succinic anhydride (2.5 g) and pyridine (12 ml) is stirred for 4 h at 100° C. under inert atmosphere. The obtained solution is cooled with addition of H$_2$O (20 ml) and HCl 6 N until pH 2, then extracted with chloroform. The organic phase is vacuum evaporated, and the residue is crystallized by benzene. 0.8 g of a white crystalline solid is obtained. M.P.=186°–8° C.; IR (KBr):1744 (RCOOAr), 1708 cm$^{-1}$ (COOH); $^1$H-NMR (CD$_3$OD) 5.35–4.90 (1H,m), 3.4–2.5 (8H,m) 2.05 (3H,s),1.95 (6H,s).

| Elemental analysis for C$_{17}$H$_{20}$O$_7$ (M.W. 336.34) | | |
|---|---|---|
|  | C % | H % |
| Eval. | 60.71 | 5.99 |
| Found | 60.87 | 5.92 |

EXAMPLE 8

(RS)-2-(2,3-dihydro-5-hydroxy-4,6,7-trimethylobenzofuranyl) acetic acid, methyl ester To a suspension of (RS)-2-(2,3-dihydro-5-hydroxy-4,6,7-trimethylbenzofuranyl) acetic acid (see example 1) (1.4 g) in diethyl ether (15 ml) is added dropwise—keeping the mixture temperature at 5° C.—an ether solution of diazomethane (prepared as in Org. Synth. Coll. Vol. II, 166), until complete dissolution of the substrate (about 20 ml is necessary). The excess diazomethane is distroyed with acetic acid. The solution is filtered and the filtrate is dried. The residue is purified by column chromatography (SiO$_2$). 1.4 g of a white crystalline solid is obtained. M.P.=108°–10° C.; IR (KBr): 3428 (OH), 1730 cm (COOMe); H-NMR (COCl$_3$) 6.5 (1H,sb), 530–4.75 (1H,m), 3.65 (3H,s), 3.35–2.55 (4H,m), 2.1 (6H,s), 2.0 (3H.s).

| Elemental analysis for C$_{14}$H$_{18}$O$_4$ (M.W. 250.29) | | |
|---|---|---|
|  | C % | H % |
| Eval. | 67.18 | 7.25 |
| Found | 67.04 | 7.26 |

EXAMPLE 6

Succinic acid, mono 5-[2,3-dihydro-2-(RS)-(methoxycarbonyl)methyl-4,6,7-trimethylbenzofuranyl]ester A mixture of (RS)-2-(2,3-dihydro-5-hydroxy-4,6,7-trimethylbenzofuranyl) acetic acid, methyl ester (see example 5) (0.25 g) and succinic anhydride (0 20 g) in pyridine (1.5 ml) is placed at 100° C. under inert atmosphere for 5 h. The thus obtained solution is cooled with addition of HCl 2 N until pH 2, and extracted with ethyl acetate. The extracts are washed twice with H$_2$O, then are dried and vacuum evaporated. The raw residue is crystallized by benzene. 0.26 g white crystalline solid is obtained. M.P. =154°–6° C.; IR (KBr): 1741 (COOAr), 1731 (COOMe), 1694 cm$^{-1}$ (COOH); $^1$H-NMR(CDCl$_3$): 10.5 (1H,sb), 5.35–4.85 (1H,m),3.7 (3H,s), 3.4–2.6 (8H,m) 2.05 (3H,s), 1.95 (6H,s).

| Elemental analysis for C$_{18}$H$_{22}$O$_7$ (M.W. 350.37) | | |
|---|---|---|
|  | C % | H % |
| Eval. | 61.71 | 6.33 |
| Found | 61.70 | 6.36 |

EXAMPLE 7

(RS)-2-(2,3-dihydro)-5-methoxy-4,6,7-trimethylbenzofuranyl) acetic acid, methyl ester To a solution of (RS)-2-(2,3-dihydro-5-hydroxy-4,6,7-trimethylbenzofuranyl) acetic acid, methyl ester (see example 5) (0.25 g) in acetone (2 ml) is added anhydrous potassium carbonate (0.15 g) and methyl iodide (0.1 ml). The mixture is refluxed for 24 h; after cooling the non-reacted potassium carbonate is filtered away and the filtrate is vacuum concentrated. The residue is subjected to chromatographic column (SiO$_2$); 60 mg of a white crystalline solid is obtained M.P.=44°–6° C.; IR (KBr): 1740 cm$^{-1}$ (COOMe); $^1$H-NMR (CDCl$_3$): 5.35–4.85 (1H,m), 3.75 (3H,s), 3.65 (3H,s), 3.4–2.5 (4H,m), 2.15 (6H,s), 2.05 (3H,s).

| Analysis for C$_{15}$H$_{20}$O$_4$ (M.W. 264.32) | | |
|---|---|---|
|  | C % | H % |
| Eval. | 68.16 | 7.63 |
| Found | 67.92 | 7.58 |

EXAMPLE 8

(a)

(RS)-2-(2,3-dihydro-5-acetyloxy-4,6,7-trimethylbenzofuranyl) acetyl chloride

To a suspension of (RS)-2-(2,3-dihydro-5-acetyloxy-4,6,7-trimethylbenzofuranyl) acetic acid (see example 2) (4.4 g) in benzene (36 ml) is added dropwise oxalyl chloride (7 ml) over 30'.

The thus obtained solution is kept under stirring at 50° C. for further 15'. After cooling, the solution is vacuum evaporated and the residue is washed twice with toluene. 4.69 g is obtained. Such product is used for the successive reactions without purification IR (KBr): 1804 cm (COCl).

(b)

(RS)-2-(2,3-dihydro-5-acetyloxy-4,6,7-trimethylbenzofuranyl) acetic acid, ethyl ester (IRFI 034)

To a solution of (RS)-2-(2,3-dihydro-5-acetyloxy-4,6,7-trimethylbenzofuranyl) acetyl chloride (1.0 g) in anhydrous tetrahydrofuran (4 ml) is added pyridine (0.4 ml), then absolute ethanol (0.3 ml); the mixture is stirred at room temperature for 1 hour. The suspension is then vacuum evaporated, and H$_2$O and ethyl acetate is added. The organic phase is dried and evaporated under vacuum. The residue is purified by column chromatography (SiO$_2$). 0.75 g of white crystalline solid is obtained. M.P.=76°–77.5° C., IR (KBr):1755 (CH$_3$COOAr), 1725 (COOC$_2$H$_5$); $^1$H-NMR (CDCl$_3$): 5.35–4.85 (1H,m), 4.2 (2H,q), 3.55–2.55 (4H,m), 2.3 (3H,s), 2.05(3H,s), 2.00 (6H,s) 1.25 (3H,t).

| Elemental analysis for C$_{17}$H$_{22}$O$_5$ (M.W. 306.36) | | |
|---|---|---|
| | C % | H % |
| Eval. | 66.65 | 7.24 |
| Found | 66.40 | 7.36 |

EXAMPLE 9
(RS)-2-(2,3-dihydro-5-acetyloxy-4,6,7-trimethylbenzofuranyl) acetic acid, isobutyl ester The working process is identical to that of example 8. The product is purified by column chromatography (SiO$_2$). 0.3 g of a white crystalline solid is obtained M.P.=44.5°–45.5° C.; IR (KBr): 1761 (CH$_3$COOAr), 1736 cm$^{-1}$ (COOR); $^1$H-NMR (CDCl$_3$): 5.35–4.85 (1H,m), 3.9 (2H,d,j=12Hz), 3.45–2.65 (5H,m), 2.3 (3H,s), 2.05 (3H,s), 2.00 (6H,s), 0.9 (6H,d,j=12Hz).

| Elemental analysis for C$_{19}$H$_{26}$O$_5$ (M.W. 334.41) | | |
|---|---|---|
| | C % | H % |
| Eval. | 68.24 | 7.84 |
| Found | 68.59 | 7.85 |

EXAMPLE 10
(RS)-2-(2,3-dihydro-5-acetyloxy-4,6,7-trimethylbenzofuranyl) acetic acid, n-octyl ester The working process is identical to that of example 8. The product is purified by column chromatography (SiO$_2$). 0.35 g of a white crystalline solid is obtained. M.P.=42.5°–43.5° C.; IR (KBr):1762 (CH$_3$COOAr), 1737 cm$^{-1}$ (COOR); $^1$H-NMR (CDCl$_3$) 5.35–4.85 (1H,m), 4.1 (2H,t), 3.55–2.65 (4H,m), 2.3 (3H,s), 2.05 (3H,s), 2.00 (6H,s), 1.6–1.1 (12H,m), 0.85 (3H,m).

| Elemental analysis for C$_{23}$H$_{34}$O$_5$ (M.W. 390.52) | | |
|---|---|---|
| | C % | H % |
| Eval. | 70.74 | 8.77 |
| Found | 70.36 | 8.76 |

EXAMPLE 11
(RS)-2-(2,3-dihydro-5-acetyloxy-4,6,7-trimethylbenzofuranyl) acetic acid, n-octadecyl ester The working process is identical to the one of example 8. The product is purified by column chromatography (SiO$_2$). 0.3 g of a white crystalline solid is obtained. M.P.=58°–58.5° C.; IR (KBr):1746 (CH$_3$COOAr), 1723 cm$^{-1}$ (COOR); $^1$H-NMR (CDCl$_3$):5.35–4.85 (1H,m), 4.1 (2H,t), 3.35–2.65 (4H,m), 2.3 (3H,s), 2.05 (3H,s), 1.95 (6H,s), 1.5:1.2 (32H,m), 0.8 (3H,m).

| Elemental analysis for C$_{33}$H$_{54}$O$_5$ (M.W. 530.79) | | |
|---|---|---|
| | C % | H % |
| Eval. | 74.67 | 10.25 |
| Found | 74.62 | 10.24 |

EXAMPLE 12
(RS)-2-(2,3-dihydro-5-acetyloxy-4,6,7,-trimethylbenzofuranyl) acetic acid, 2-dimethylamino ethyl ester, chlorhydrate To a solution of (RS)-2-(2,3-dihydro-5-acetyloxy-4,6,7-trimethylbenzofuranyl) acetyl chloride (see example 8) (0.3 g) in anhydrous tetrahydrofuran (1 ml) there is added N,N-dimethylethanolamine (0.09 ml). The reaction mixture is kept under stirring for 1 h; the obtained precipitate is vacuum filtered, washed with diethyl ether, dried and crystallized by ethyl acetate. 0.25 g of a white crystalline solid is obtained. M.P.=166°–8° C.; IR (KBr):2650 (NH), 1752 (CH$_3$COOAr), 1742 cm$^{-1}$ (COOR); $^1$H-NMR (CD$_3$OD): 5.4:4.8 (1H,m) 4.5:4.3 (2H m), 3.65–2.75 (6H,m), 2.9 g (6H,s), 2.3 (3H,s), 2.05 (3H,s), 1.95 (6H,s).

| Elemental analysis for C$_{19}$H$_{28}$ClNO$_5$ (M.W. 385.89) | | | |
|---|---|---|---|
| | C % | H % | N % |
| Eval. | 59.14 | 7.31 | 3.63 |
| Found | 58.93 | 7.38 | 3.60 |

EXAMPLE 13
(RS)-2-(2,3-dihydro-5-acetyloxy-4,6,7-trimethylbenzofuranyl) acetic acid 2-(4-morpholin) ethyl ester, hydrochlorate To a solution of (RS)-2-(2,3-dihydro-5-acetyloxy-4,6,7-trimethylbenzofuranyl) acetyl chloride (see example 8) (S.4 g) in anhydrous tetrahydrofuran (10 ml) is added 4-(2-hydroxyethyl) morpholine (1.3 ml). After 1 h the resulting precipitate is vacuum filtered. The purification of the product takes place by extraction with diethyl ether of the aqueous solution of the chlorhydrate brought to pH 7 with 5% sodium bicarbonate.

The extracts are dried, vacuum concentrated and treated with diethyl ether saturated with HCl.

The precipitate is then vacuum filtered, dried and re-crystallized by an ethyl acetate and methanol mixture. 2.8. g of a crystalline solid is obtained. M.P.=161°–3° C.; IR (KBr):2556, 2455 (NH), 1753 (CH$_3$COOAr), 1738 cm$^{-1}$ (COOR); $^1$H-NMR (CD$_3$OD): 4.8:5.4 (1H,m), 4.6:4.35 (2H,t), 4.15:3.7(4H,t), 3.6:2.6 (10H,m) 2.3 (3H,s), 2.05(3H,s), 1.95 (6H,s).

| Elemental analysis for C$_{21}$H$_{30}$ClNO$_6$ (M.W. 427.92) | | | |
|---|---|---|---|
| | C % | H % | N % |
| Eval. Found | 58.94 | 7.07 | 3.27 |

We claim:
1. A compound of formula:

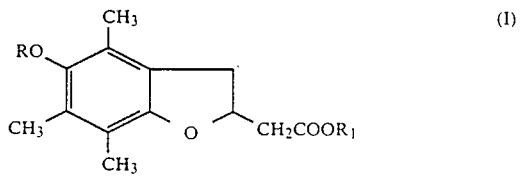

(I)

or its pharmaceutically acceptable salts, wherein R is:
hydrogen;

acyl, either linear or branched, with a number of carbon atoms variable from 1 to 7,
hemiacyl of a dicarboxylic acid,
lower alkyl,
$R_1$ is:
hydrogen,
linear or branched alkyl with 2 to 20 carbon atoms,
alkyl either of the type:

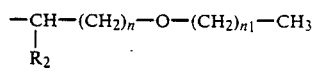

wherein n and $n_1$ are number variable for 0 to 6 and $r_2$ is lower alkyl,
alkyl diether of the type:

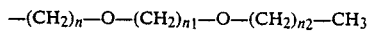

wherein n, $n_1$ are variable from 1 to 6 and $n_2$ is a number variable from 0 to 6,
alkylamine of the type:

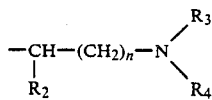

wherein n is a number variable from 0 to 6, $R_2$ has the previous meaning and $R_3$ and $R_4$ are lower alkyls,
and N-alkylheterocyclic of the type:

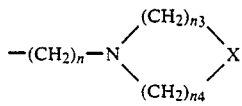

wherein $X=CH_2, S, O, NR_2$;
$R_2$ has the previous meaning, n is a number variable from 1 to 6 and $n_3$ and $n_4$ are numbers variable from 1 to 3.

2. A compound of claim 1, wherein R is: acetyl, propanoyl, butanoyl, isobutanoyl, hemisuccinoyl, methyl or ethyl; and $R_1$ is: hydrogen, ethyl, isobutyl, octyl or octadecyl.

3. A compound according to claim 1, wherein $R_1$ is dimethylaminoethyl, or an N-ethylmorpholinic or an N-ethyl-N'-methylpiperazinic group.

4. The compound of claim 1, wherein R is acetyl and $R_1$ is hydrogen.

5. Pharmaceutical compositions having antiinflammatory, mucolytic and mucoregulating activity, containing the compound of claim 1 as active drug with a non-toxic conventional pharmaceutical excipient.

* * * * *